United States Patent [19]

Cosentino et al.

[11] 4,163,722
[45] Aug. 7, 1979

[54] UNIVERSAL DIALYZER END CAP

[75] Inventors: Louis C. Cosentino, Wayzata; Louis Seiler, Minneapolis; Richard A. Helms, Elk River, all of Minn.

[73] Assignee: Renal Systems, Inc., Minneapolis, Minn.

[21] Appl. No.: 877,620

[22] Filed: Feb. 14, 1978

[51] Int. Cl.² ............................................. B01D 31/00
[52] U.S. Cl. ................................. 210/236; 210/321 B; 210/494 M
[58] Field of Search ........... 210/321 A, 321 B, 321 R, 210/494 M, 236

[56] References Cited

U.S. PATENT DOCUMENTS

| | | | |
|---|---|---|---|
| 3,390,779 | 7/1978 | Kumme et al. | 210/321 B |
| 3,712,474 | 1/1973 | Martinez | 210/494 M X |
| 3,743,098 | 7/1973 | Martinez | 210/321 B |
| 3,985,655 | 10/1976 | Miller | 210/494 M X |
| 4,008,157 | 2/1977 | Miller et al. | 210/494 M X |

Primary Examiner—Frank A. Spear, Jr.
Attorney, Agent, or Firm—Schroeder, Siegfried, Ryan, Vidas & Steffey

[57] ABSTRACT

A universal dialyzer end cap which provides a connection between a kidney dialyzer and a blood tubing line. The end cap is constructed of a material which allows a firm connection to the dialyzer while at the same time is of a configuration which does not allow blood to contact the surface of the end cap when properly attached to a kidney dialyzer.

6 Claims, 4 Drawing Figures

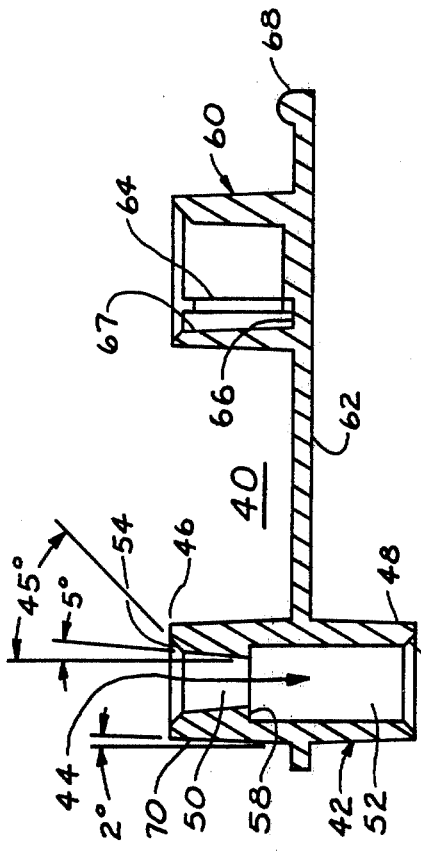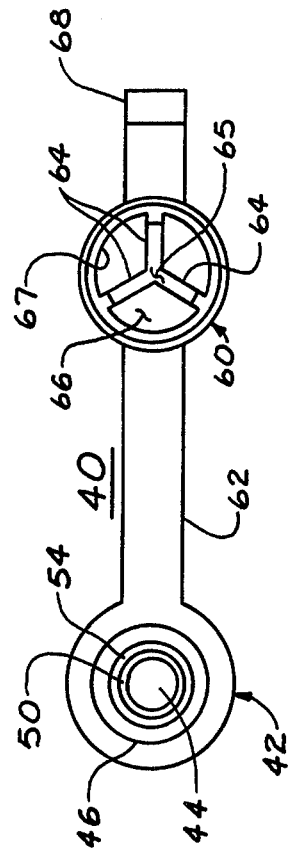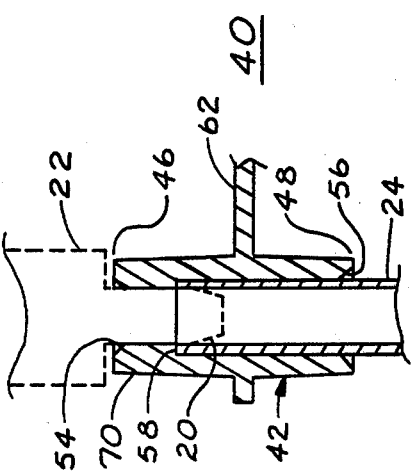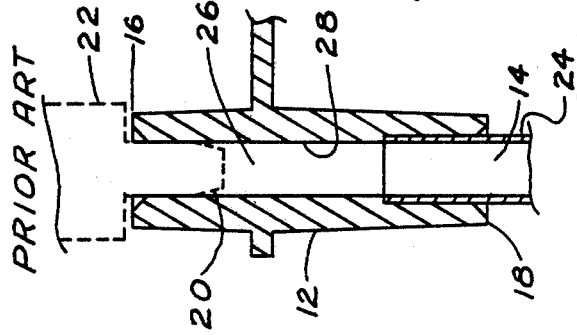

UNIVERSAL DIALYZER END CAP

BACKGROUND

In kidney dialysis treatment a connection must be made between the kidney dialyzer and the blood tubing set through which the patient's blood passes. This invention relates to a universal dialyzer end cap which provides a firm physical connection between the dialyzer and the blood tubing set while at the same time the patient's blood is not allowed to contact the inner surface of the end cap.

End caps are provided on the end of blood tubing sets for connecting the blood line to a nipple on an artificial kidney dialyzer. Prior art end caps are typically configured such that the end cap has an opening at one end for receiving the nipple and an opening at the other end into which the blood tubing line is permanently secured. However, the dimensions and fit are such that the end of the nipple does not actually extend into the blood line so that there is a gap between the end of the nipple and the blood line. Most end caps and blood tubing have been made of a material such as polyvinyl chloride (PVC) which contains a significant amount of plasticizers and lubricant. In addition PVC has certain thrombogenicity characteristics which make it undesirable for contact with blood. Because of the gap between the nipple and the tubing line in prior art end caps, blood flowing through the dialyzer contacts the PVC inner surface of the end cap and the PVC blood line. Because of the undesirable plastisizers and lubricant and the thrombogenicity characteristics of PVC this contact is highly undesirable.

One solution to this problem has been the introduction of blood tubing and end caps made of a polyurethane thermoplastic polymer sold by Renal Systems, Inc. under the trademark RENATHANE®. This urethane polymer is less thrombogenic than PVC and contains no plasticizers and little lubricant compared to PVC. Costwise, however, urethane is much more expensive than PVC.

The present invention offers another solution to the problem by providing a universal dialyzer end cap which is made of PVC but is configured such that the nipple of a kidney dialyzer when inserted in one end of the end cap is firmly force fit so as to extend into the blood tubing line. In this way the desirable mechanical properties of PVC provide a tight connection between the nipple of the dialyzer and the end cap on the blood tubing set while at the same time, blood flows through the nipple and directly into the blood tubing line. If a urethane blood tubing line or a line having at least a urethane inner lining is employed, blood never contacts the inner surface of the end cap which is PVC. Therefore the present invention provides an end cap which is safer and more biocompatible from the patient's standpoint. Another feature of the present invention is that the end cap opening that receives the nipple has a narrowing taper to conform more closely to the nipple. As the end cap is pushed into the nipple the PVC expands to cause a tight grip. This action coupled with the expansion of the urethane tubing line, caused by entry into the tubing line of the nipple creates a banding effect to make the grip of the urethane tubing line on the nipple even greater. Another advantage of the present invention is that the opening which receives the dialyzer nipple, has a 30° chamfer to facilitate entry. The end cap of the present invention is provided with a closure such that gases are allowed to the interior of the tubing set to achieve adequate sterilization by well known sterilization processes utilizing ethylene oxide as the sterilizing agent. The closure maintains the interior of the tubing set clean before, during and after sterilization. Sterility is maintained by using appropriate packaging, such as a gas-permeable tubing set pouch that is impermeable to bacteria.

SUMMARY OF THE INVENTION

The present invention provides a universal dialyzer end cap comprising a member having an elongated opening passing therethrough. One end of the opening is adapted to receive a nipple of a kidney dialyzer and the other end of the opening is adapted to have permanently secured therein a blood tubing line. The opening is configured such that when the one end is secured on a nipple, the nipple is force fit into the blood line to provide a tight connection and such that blood flowing through the end cap is not able to contact the inner surface of the end cap. Both ends of the end cap are provided with an approximately 45° chamfer to facilitate entry. Also the nipple receiving end of the end cap is provided with a narrowing taper. A closure integrally formed with the end cap is provided to maintain the cleanliness of the interior after appropriate sterilization until used. The closure is constructed in such a way as to allow gas passage which is necessary during sterilization when the closure is in place.

BRIEF DESCRIPTION OF THE DRAWINGS

FIG. 1 is a cross-sectional view of an end cap of the prior art;

FIG. 2 is a cross-sectional view of an end cap of the present invention;

FIG. 3 is a top view of the end cap shown in FIG. 2; and

FIG. 4 is a cross-sectional view of the end cap of the present invention connected to the nipple of a dialyzer and having a blood tubing lined secured therein.

DETAILED DESCRIPTION

FIG. 1 shows a typical prior art end cap 10 in cross-section. End cap 10 comprises a tubular member 12 having an opening 14 passing completely therethrough from one end 16 to the other end 18 thereof. Opening 14 is smaller in cross-sectional diameter at end 16 than at end 18.

End cap 10 is shown connected to a nipple 20 of dialyzer 22 (both shown dotted) at end 16. Permanently secured in end 18 of cap 10 is a blood tubing line 4. As can be seen when fully inserted into end 16, nipple 20 does not reach or extend into tubing line 24, thus defining a gap 26 between the end of nipple 20 and tubing line 24.

Typically cap 10 is made of a PVC material which has undesirable thrombogenic characteristics and contains plasticizers and lubricant. As a result blood passing through end cap 10 will contact the inner surface 28 of cap 10 exposing the blood to the poor thrombogenicity characteristics of PVC, the plasticizers and lubricant. This blood-to-PVC contact is neither good from the viewpoint of patient safety nor biocompatibility. Further since nipple 20 does not extend into tubing line 24, the physical connection between cap 10 and nipple 20 is not as tight or firm as is desirable to insure that the tubing line does not separate from the dialyzer during dialysis of a patient.

FIG. 2 shows in cross-section an end cap 40 of the present invention. End cap 40 comprises a tubular member 42 having an opening 44 passing completely therethrough from one end 46 to the other end 48 of member 42. Opening 44 is made up of two sections—nipple receiving section 50 and tubing line receiving section 52. Both ends 46 and 48 of opening 44 have an approximately 45° chamfer shown at 54 and 56 respectively to facilitate entry by a kidney dialyzer nipple in end 46 and a tubing line in end 48. Section 50 has a narrowing taper of approximately 5° which extends from the inner end of chamfer 54 toward section 52. This 5° taper is provided to generally conform to the taper most typically provided on a kidney dialyzer nipple. The cross-sectional diameter of section 52 is greater than the cross-sectional diameter of section 50 of opening 44. Section 52 is sized to accommodate the size of blood tubing line which is permanently secured therein as seen in FIG. 4. By section 52 having a greater cross-sectional diameter the section 50, when tubing line 24 is inserted into section 52, the end of line 24 abuts against ridge 58.

Molded integrally with member 42 is a closure 60 which is connected to the member 42 by extension 62. Closure 60 is designed to fit over end 46 of member 42. The inside surface of closure 60 has three ridges 64 integrally molded therewith as seen in FIG. 3, which is a top view of the end cap 40. Ridges 64 extend from the same point 65 on bottom inside surface 66 of closure 60 and along the inside wall 67 of closure 60. Closure 60 has a tab 68 formed integrally therewith to permit closure 60 to be easily removed from end 46 of member 42. The outer surface 70 of end 46 of member 40 has a slight taper of approximately 2°. This taper on outer surface 70 facilitates seating closure 60 over end 46 of member 42. Ridges 64 provide a tight fit over end 46 when closure 60 is so seated, while at the same time allowing a gas passage from opening 44 between closure 60 and outer surface 70 during sterilization as will be explained below.

End cap 40 is preferably made of a PVC material having a Shore Durometer of approximately 65A to 70A. However, other materials having similar hardness and mechanical properties may be employed. Preferably end cap 40 is a single molded piece but it may also be made by other means. Although closure 60 is molded integrally with member 42 for ease of handling and to prevent losing the parts, they could be made as separate pieces.

After the manufacture of end cap 40 has been completed, in preparation for sterilization, closure 60 is placed over end 46 of member 42. In this way a gas passage is provided which is necessary for ethylene oxide sterilization. Closure 60 remains in place over end 46 until end cap 40 is removed from its sterile package. Closure 60 maintains the cleanliness of the interior of end cap 40 until ready for use. In most cases blood tubing line 24 is permanently secured in position as seen in FIG. 4. Line 24 and member 42 may be solvent bonded together with tetrahydrofuran to form a polymeric weld. Other solvent/cement systems may also be used provided a firm weld is achieved.

When ready for use closure 60 (not shown in FIG. 4) is removed from end 46 of member 42 and end 46 is forced onto nipple 20 of dialyzer 22 (shown dotted). The end of nipple 20 spreads section 50 of opening 42 and enters into tubing line 24 as seen in FIG. 4. With the insertion of nipple 20 into section 50, member 42 expands thereby causing a gripping action on nipple 20. The entry of the end of nipple 20 into tubing line 24 also causes an expansion of the line 24 and together with the expansion of member 42 creates a banding effect. This banding effect makes the grip of the tubing line 24 contact surface greater so as to greatly reduce the likelihood of the end cap separating from the dialyzer nipple during use.

Preferably the tubing line used is a polyurethane such as RENATHANE ® tubing as made by Renal Systems, Inc. Tubing line made of other biocompatible materials could also be used. With the construction of the present invention, the blood flowing through the dialyzer and the tubing line never contact the inner surface of member 42. This construction allows the desirable mechanical properties of PVC for the end cap to be used to achieve a tight physical connection to the nipple of the dialyzer while at the same time allowing the blood to contact only surfaces which are biocompatible in that the surfaces contacted by the blood are highly nonthrombogenic, have no plasticizers and much less lubricant than materials such as PVC.

Although end cap 40 and tubing line 24 are shown in FIG. 4 as an integral item, it should be recognized that the end cap 40 could be made without direct attachment to any particular blood tubing line at the time of manufacture. End cap 40 could be used with any type of blood tubing line.

Although a preferred embodiment of the invention has been disclosed, many modifications may be made without departing from the spirit and scope of the invention as claimed.

We claim:

1. A universal dialyzer end cap comprising: a member having an elongated opening passing completely therethrough, one end of said opening adapted to receive a nipple of a kidney dialyzer and the other end of said opening adapted to have permanently secured therein a blood tubing line; said one end of said opening having a cross-sectional diameter which is smaller than the cross-sectional diameter of said other end, said one end of said opening having a narrowing taper of approximately 5° extending partially toward said other end of said opening such that when said one end is secured on a nipple of a dialyzer and said other end has a blood tubing line secured therein, the nipple will be firmly force fitted into the blood line to provide a tight connection and such that blood flowing between the dialyzer and the blood line is not able to contact the inner surface of said member.

2. An end cap as set forth in claim 1 wherein said member is made of a polyvinyl chloride polymer having a Shore Durometer in the range of approximately 65 to 75A to insure a firm fit with the nipple.

3. An end cap as set forth in claim 1 wherein said one and said other ends each has an approximately 45° chamfer to facilitate entry therein.

4. An end cap as set forth in claim 1 further comprising a closure integrally formed with said member, said closure being constructed to fit over said one end of said opening so as to allow air passage and for maintaining the sterility of the interior of said member after appropriate sterilization.

5. In a blood tubing set including a blood tubing line and dialyzer end cap having an opening passing completely therethrough from one end to the other end and which has permanently secured in one end of said opening thereof said line, the improvement comprising:

said other end of said opening having a cross-sectional diameter which is less than the cross-sectional diameter of said one end, said other end of said opening having a narrowing taper of approximately 5° extending part way toward said one end of said opening and being adapted to receive a nipple of a kidney dialyzer, said narrowing taper being of a length such that when the nipple is received in said other end of said opening, the nipple is force fit into the blood line to provide a tight connection and such that blood flowing between the dialyzer and the blood line is not able to contact the inner surface defined by the opening passing through said end cap.

6. In a blood tubing set as set forth in claim 5 wherein: said end cap is made of a polyvinyl chloride polymer; and at least the inner surface of said tubing line is made of a polyurethane themoplastic polymer, so that when the dialyzer nipple is inserted in said other end of said opening, the end cap and tubing line both expand to create a banding effect which greatly increases the grip of the end cap and tubing line contact surfaces with the nipple.

* * * * *